(12) United States Patent
Brunner et al.

(10) Patent No.: US 8,538,505 B2
(45) Date of Patent: Sep. 17, 2013

(54) METHOD FOR 3-D DATA COLLECTION WITH A BIPLANE C-ARM SYSTEM WITH BIPLANE ACQUISITION MULTIPLEXING

(75) Inventors: Thomas Brunner, Nürnberg (DE); Sebastian Graf, Greding (DE); Bernd Schreiber, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 467 days.

(21) Appl. No.: 12/855,758

(22) Filed: Aug. 13, 2010

(65) Prior Publication Data

US 2011/0040178 A1      Feb. 17, 2011

(30) Foreign Application Priority Data

Aug. 13, 2009 (DE) .................... 10 2009 037 478

(51) Int. Cl.
*A61B 5/055* (2006.01)
*A61B 6/03* (2006.01)

(52) U.S. Cl.
USPC ............................................. 600/428; 378/9

(58) Field of Classification Search
None
See application file for complete search history.

(56) References Cited

U.S. PATENT DOCUMENTS

| | | | |
|---|---|---|---|
| 5,515,416 A * | 5/1996 | Siczek et al. | 378/197 |
| 6,435,713 B1 * | 8/2002 | Iizuka | 378/195 |
| 7,187,745 B2 | 3/2007 | Flohr | |
| 7,220,052 B2 | 5/2007 | Gotoh | |
| 7,379,532 B2 | 5/2008 | Kramp | |
| 7,500,784 B2 | 3/2009 | Grebner | |
| 7,594,751 B2 * | 9/2009 | Grebner et al. | 378/197 |
| 7,789,562 B2 * | 9/2010 | Strobel | 378/207 |
| 8,059,874 B2 * | 11/2011 | Pfister et al. | 382/128 |
| 2002/0181645 A1 * | 12/2002 | Bruder et al. | 378/8 |
| 2004/0097806 A1 | 5/2004 | Hunter | |
| 2005/0203386 A1 * | 9/2005 | Heigl et al. | 600/427 |
| 2006/0067459 A1 | 3/2006 | Boese | |
| 2006/0083351 A1 * | 4/2006 | Lamberty et al. | 378/86 |
| 2008/0187092 A1 | 8/2008 | Boese | |
| 2009/0207968 A1 * | 8/2009 | Grass | 378/9 |
| 2011/0274246 A1 * | 11/2011 | Maschke | 378/62 |

FOREIGN PATENT DOCUMENTS

| | | |
|---|---|---|
| DE | 10119226 A1 | 12/2002 |
| DE | 102006056687 A1 | 5/2008 |
| WO | WO 2007149750 A2 | 12/2007 |

OTHER PUBLICATIONS

Siemens AG, Medical Solutions—Angiography, Fluoroscopic and Radiographic Systems Introducing Artis zee for cardiac procedures—There's so much more to zee. © Jan. 2008, Siemens AG; Order No. A91AX-10805-11C1-7600, CC AX 10805 WS 01081.7.

* cited by examiner

*Primary Examiner* — Long V. Le
*Assistant Examiner* — Angela M Hoffa

(57) ABSTRACT

A method for collecting three-dimensional data of an object from a series of projection images recorded by a biplane C-arm system is provided. A cardiac activity is recorded. The cardiac frequency and a start cardiac phase are determined for calculating parameters of the C-arm planes. The C-arm planes are set with the parameters and data is acquired in the start cardiac phase. The C-arm planes are uniformly rotated at a same speed in a forward motion over an angular area and record data at different angular areas at different cardiac phases. Data is acquired in the start cardiac phase after termination of the forward motion. The C-arm planes are uniformly rotated at a same speed in a backward motion over an angular area and records data at different angular areas at different cardiac phases. The captured data are reconstructed after termination of the backward motion upon completed acquisition.

8 Claims, 7 Drawing Sheets

METHOD FOR 3-D DATA COLLECTION WITH A BIPLANE C-ARM SYSTEM WITH BIPLANE ACQUISITION MULTIPLEXING

CROSS REFERENCE TO RELATED APPLICATIONS

This application claims priority of German application No. 10 2009 037 478.7 filed Aug. 13, 2009, which is incorporated by reference herein in its entirety.

FIELD OF THE INVENTION

The invention relates to a method for 3-D data collection by means of a series of projection images of an object to be examined from different recording angles during a rotation run with a biplane C-arm system with two separate C-arm planes, where three-dimensional image data can be reconstructed from the projection images. Methods of this kind can serve to effect triggered cardiac reconstruction on the computer tomography C-arm system with biplane acquisition.

BACKGROUND OF THE INVENTION

In the cardiac systems used to date, the 3-D cardiac acquisition always takes place using an individual C-arm plane and employing software known as DynaCT-Cardiac.

Here, the C-arm is rotated in four rotation runs (two forward and two backward runs) by 200° in each case around the patient. The need for an acquisition of an angular area of 200° results from the geometrical properties of a fan emitter. This makes it necessary, for clean reconstruction, to record over 200° (180°+fan angle) instead of 180°.

During this rotational movement data is in each case acquired. By means of an ingenious selection of the starting points of the individual rotation runs, depending on the cardiac phase and cardiac frequency of the patient, the recordings can be controlled in such a way that a reconstruction of the heart at a particular cardiac phase can be generated from the totality of the data. This takes place through the existence of matching recordings from all angles necessary for reconstruction, that is complete coverage of the recording area. Through the use of four rotation runs a corridor of ±0.125 cardiac phases around the desired reconstruction cardiac phase can be achieved. In the case of secondary reconstructions at other cardiac phases impaired image quality may result, as the error of the corridor can increase to ±0.25 cardiac phases.

Because of the need for four rotation runs for clean coverage of all areas, a further disadvantage arises in the case of the previously cited method through additional overhead. The C-arm plane must be accelerated four times, braked once again and especially also re-started at the switching points, triggered on the basis of a specific cardiac phase. Massive delays can thereby occur, which in turn calls for a longer injection of contrast medium.

Even in the case of biplane systems in 3-D-Cardiac, which already boast two independent planes, only one C-arm plane (plane A) is employed in this acquisition. The second C-arm plane is moved from the acquisition area into a parking position and thus not currently used for 3-D data capture.

From US 2008/0187092 A1 a method for 2-D-imaging, in particular ECG-triggered fluoroscopy, is known, in which to determine a multiplicity of ECG-triggered recording moments for imaging, the following steps are executed in respect of a heart to be mapped: Recording of a multiplicity of images of the heart at previously prescribed temporal intervals; assignment of the images to specific cardiac phase moments; comparison of the images to determine similarity measures, which represent similar image-related states of the heart to be imaged, between two images in each case; identification of a group of images with mutual similarity measures in a prescribed area, between the pairs of images; and definition of the cardiac phase moments belonging to the images in the group as the multiplicity of ECG-triggered recording moments. In a further aspect, the method can additionally contain the step for execution of moving imaging on the basis of recordings at the specific recording moments based on an ECG-triggering.

US 2004/0097806 A1 describes an image-guided catheter navigation system, in which an icon, which represents a catheter, is superimposed on the image in the current catheter position.

DE 10 2006 056 687 A1 relates to a method for the recording and representation of electro anatomical images of the heart, in which a multi-electrode catheter is introduced for the simultaneous recording of multiple intracardial electrocardiograms in the area of the heart which is of interest. During the recording of the intracardial electrocardiograms a 3-D-image data record of the heart is recorded with a tomography-capable imaging device. This electrical and anatomical information from the heart is then overlaid.

SUMMARY OF THE INVENTION

The invention is based on the problem of embodying a method such as that cited in the preamble, such that the use of both C-arm planes accelerates the process and thus the acquisition time is significantly reduced.

According to the invention, the problem is solved by the features specified in independent claim. Advantageous embodiments are specified in the dependent claims.

In the abovementioned method, this is achieved by means of the following steps:
a) Recording of the cardiac activity by means of an ECG,
b) Determining of the cardiac frequency of the object to be examined and calculation of a start cardiac phase,
c) Calculation of parameters for the C-arm planes from the values determined according to step b) and setting of the parameters,
d) Start of the acquisition of data in the start cardiac phase after ensuing setting of the parameters,
e) Uniform rotation of both C-arm planes at the same speed in a first direction of rotation as forward motion over an angular area and recording of different angular areas of the patient during different cardiac phases,
f) Start of acquisition of the data after termination of the forward motion in the start cardiac phase,
g) Uniform rotation of both C-arm planes at the same speed in a second direction of rotation as backward motion over an angular area and recording of different angular areas of the patient during different cardiac phases, and
h) Reconstruction of the captured data after termination of the backward motion in the case of completed acquisition.

A method of this kind with biplane acquisition multiplexing enables particularly rapid triggered cardiac reconstruction on CT C-arm systems.

According to the invention, step c) can have the following features:
c1) Calculation of an intermediate angle of the C-arm planes.
c2) Positioning of one of the C-arm planes in such a way that these are located at the distance of the intermediate angle.
c3) Alignment of the C-arm planes with the calculated start cardiac phase.

In an advantageous manner, the first C-arm plane A can be positioned according to step c2).

It has proved to be advantageous if the angular area according to the steps e) and g) amounts to 200°+"min. intermediate angle".

Alternatively according to the invention step c) can have the following features:

c) Calculation of the necessary speed of rotation of the entire system.

It has proved to be advantageous if the angular area according to the steps e) and g) amounts to 200°−"min. intermediate angle".

In an advantageous manner a cyclical, sequential arrangement of the sequence of the angular areas can take place, where the sequence of the angular areas can proceed in the following manner:

1. C-arm plane A: forward motion
2. C-arm plane A: backward motion
3. C-arm plane B: forward motion
4. C-arm plane B: backward motion

BRIEF DESCRIPTION OF THE DRAWINGS

The invention is explained in greater detail below on the basis of the exemplary embodiments represented in the drawing. Wherein.

DETAILED DESCRIPTION OF THE INVENTION

Figure 1:
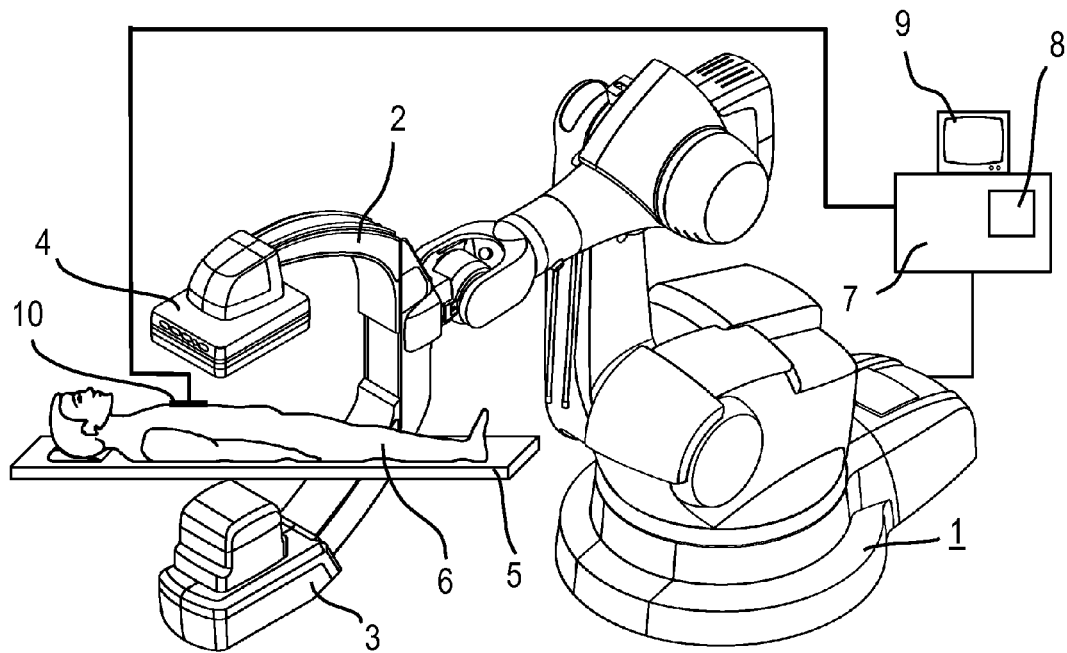
FIG. 1 Shows a known X-ray C-arm system with a industrial robot as the carrier apparatus, FIG. 2 Shows a view of the path of a detector and a radiation source according to FIG. 1 around an object to be examined in an axial perspective, FIG. 3 Shows a compact representation of the fan distribution over the entire scan area, FIG. 4 Shows the worst-case scenario of the acquisition with an intermediate angle of 75°, FIG. 5 Shows an unfavorable case of an optimized variant with a changed beginning of the acquisition and the resultant lesser intermediate angle of now just 50°, FIG. 6 Shows the optimum case of the distribution in the case of an intermediate angle of 33.33° and a resultant overall angle of rotation of 166.66°, FIG. 7 Shows a "mixed solution", in which one fan remains unused, with a intermediate angle of 36,36° and a resultant overall angle of rotation of 181.82°, FIG. 8 Shows a simulation run with a reconstruction time $\tau_{REC}$=0.25 at a cardiac frequency of 47 bpm, FIG. 9 Shows a distribution of the cardiac phases used for primary reconstruction in the case of a desired cardiac phase of 0.75, FIG. 10 Shows a simulation run with a reconstruction time $\tau_{REC}$ =0.75 and at a cardiac frequency of 60 beats per minute with an intermediate angle of 33.33°, FIG. 11 Shows a biplane angio C-arm system having two separate C-arm planes, and FIG. 12 Shows a view of paths of the two detectors and the two radiation sources according to FIG. 11 around an object to be examined in axial perspective.

FIG. 1 shows an X-ray diagnostic device, having a C-arm 2 rotatably mounted on a stand in the form of a six-axes industrial robot or articulated-arm robot 1, on the end of which are arranged an X-ray irradiation source, for example an X-ray radiator 3, and an X-ray image detector 4 as an image recording unit.

By means of the articulated-arm robot 1 for example known from U.S. Pat. No. 7,500,784 B2, which preferably has six axes of rotation and thus six degrees of freedom, the C-arm 2 can be spatially adjusted at will, by, for example, being rotated about a center of rotation between the X-ray radiator 3 and the X-ray detector 4. The inventive X-ray system 1 to 4 is in particular rotatable about fulcrums and axes of rotation in the C-arm plane of the X-ray image detector 4, preferably about the center point of the X-ray image detector 4 and about axes of rotation intersecting the center point of the X-ray image detector 4.

The known articulated-aim robot 1 has a base frame, which is for example permanently mounted on a floor. To this is affixed a carousel rotatable about a first axis of rotation. On the carousel is arranged a robot rocker atm rotatable about a second axis of rotation, to which is attached a robot arm rotatable about a third axis of rotation. At the end of the robot arm is arranged a robot hand rotatable about a fourth axis of rotation. The robot hand has a fixing element for the C-arm 2, which can be pivoted about a fifth axis of rotation and is rotatable about a sixth axis of rotation running perpendicular to this.

The realization of the X-ray diagnostic device does not rely on the industrial robot. Customary C-arm devices can also be employed.

The X-ray image detector 4 can be a rectangular or square, flat semiconductor detector, which is preferably created from amorphous silicon (a-Si).

In the beam path of the X-ray radiator 3, a patient 6 to be examined is positioned on a patient couch 5 for the recording for example of a heart, as the object to be examined. Connected to the X-ray diagnostic device is a system control unit 7 with an image system 8, which receives and processes the image signals from the X-ray image detector 4. The X-ray images can then be viewed on a monitor 9.

Sensors 10, which are for example applied to the rib cage of the patient 6, can record the ECG signals of the patient 6 and transmit them to the system control unit 7.

Figure 2:
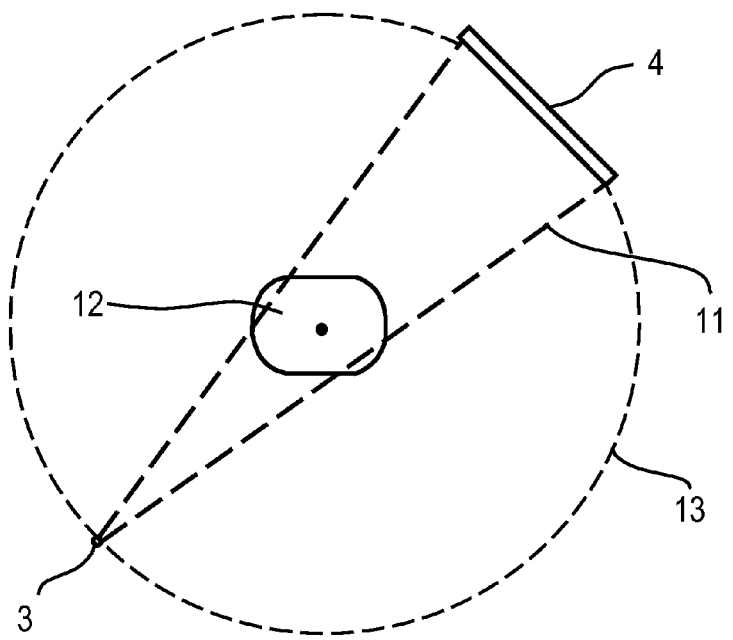

The X-ray radiator 3 emits a beam bundle 14 emerging from a beam focus of its X-ray irradiation source, which strikes the X-ray image detector 4. If 3-D data records are to be created using the so-called DynaCT-method, the rotatably mounted C-arm 2 with X-ray radiator 3 and X-ray image detector 4 are rotated in such a way that as FIG. 2 shows, schematically looking at the axis of rotation, the X-ray radiator 3 here pictorially represented by its beam focus and the X-ray image detector 4 move on an orbit 13 around an object to be examined 12 which is located in the beam path 11 of the X-ray radiator 3. The orbit 13 can be completely or partially traversed in order to create a 3-D data record.

The C-arm 2 with X-ray radiator 3 and X-ray image detector 4 here moves according to the DynaCT-method preferably around at least an angular area of 180°, for example 180° plus fan angle, and in quick succession takes projection images from different projections. The reconstruction can only take place from a subarea of this captured data.

The object to be examined 12 can for example take the form not just of an animal or human body but also a phantom body.

The X-ray radiator 3 and the X-ray image detector 4 in each case circle the object 12 in such a way that the X-ray radiator 3 and the X-ray image detector 4 lie on opposite sides of the object 12.

In the case of the normal radiography or fluoroscopy by means of a an X-ray diagnostic device of this type, the medical 2-D data from the X-ray image detector 4 is buffered if appropriate in the image system 8 and subsequently displayed on the monitor 9.

If X-ray diagnostic devices of this type are now to be employed as biplane C-arm systems with two separate C-arm planes, then for example two of the described C-arm systems with articulated-arm robot 1 can be combined.

Figure 11:
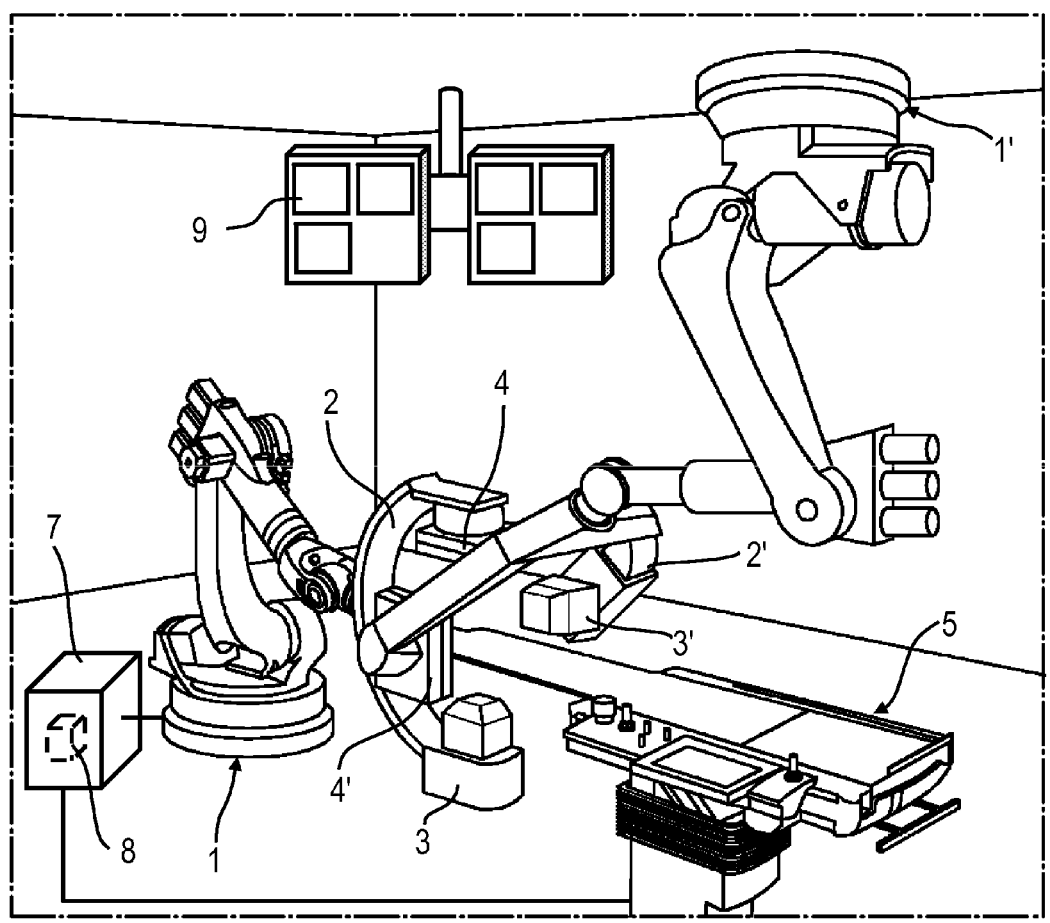
Figure 12:
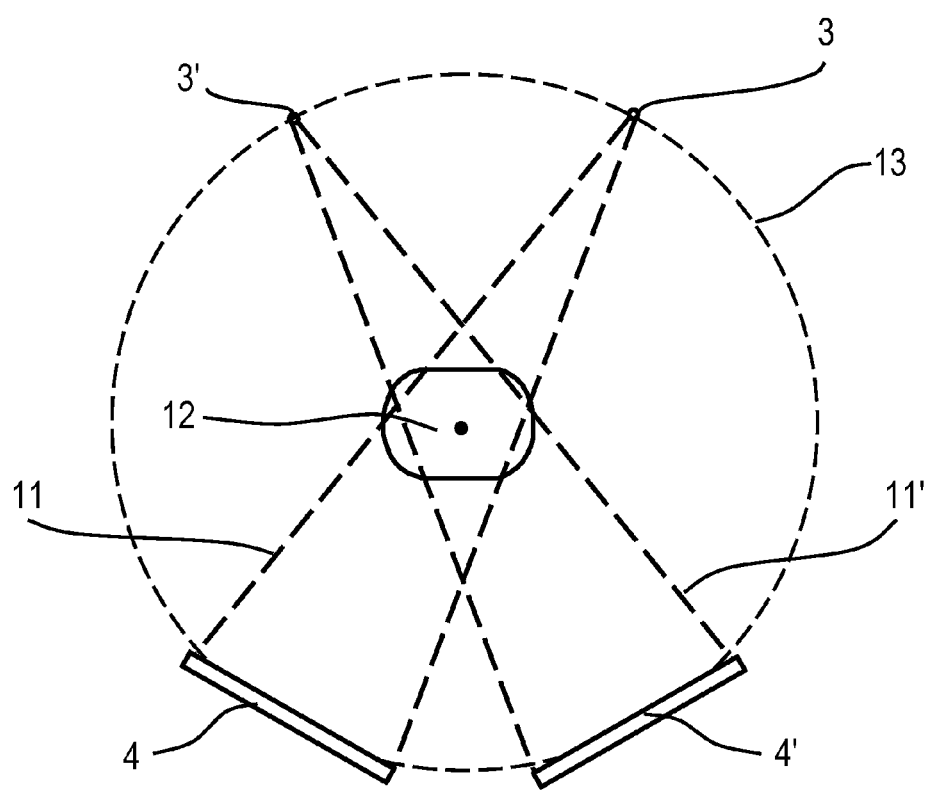

FIG. 11 shows a biplane angio C-arm system having two separate C-arm planes. An articulated-arm robot 1' is mounted on the ceiling. A C-arm 2' is mounted on the robot arm F. An X-ray radiator 3' and an X-ray image detector 4' are arranged on the C-arm 2'. Biplane angio systems can also be employed to perform 3-D cardiac acquisitions of this type, such as are for example shown in the brochure "Introducing Ards zee for cardiac procedures.- There's so much more to zee." from Siemens AG, Medical Solutions - Angiography, Fluoroscopic and Radio-graphic systems, which can be mounted on the floor and/or the ceiling. FIG. 12 shows a view of a beam path 11 of the X-ray radiator 3 and a beam path 11' of the X-ray radiator 3' according to FIG. 11 around an object 12 to be examined in axial perspective.

The main problem of a cardiac acquisition lies in the arrangement, the coordination and the linkage of the individual runs, in order to enable a good reconstruction of a desired cardiac phase. These must be controlled in such a way that complete coverage of the recording area with projections, generated for the desired reconstruction cardiac phase, is guaranteed. This difficulty also represents a challenge in using both C-arm planes. Furthermore, the use of two C-arm planes must in no way render the temporal resolution worse than in the current realization, and a clear reduction of the acquisition time should also be achieved through parallelization of the recordings and minimization of the overhead.

At the same time in a second embodiment the maximum angle of rotation of the second C-arm plane is to be regarded as a critical parameter, and minimized.

1. First Inventive Solution Approach

In a first inventive solution approach the problem is addressed by means of a fan-like division of the recording area into angular areas of the same size. These angular areas are then assigned to the different C-arm planes in a selective manner and linked to fog in an overall acquisition through coordinated dovetailing (Multiplexing (MUX)) of the individual recordings. By means of this technique it is possible in future to realize a recording equivalent in quality to DynaCT Cardiac with just two runs instead of with four, using both C-arm planes. The C-arm planes for their part rotate simultaneously at the same speed of rotation in the same direction; they accordingly have a fixed angle to each other, hereinafter referred to as an intermediate angle.

1.1. Fan Definition

The whole recording area, because of the fan beam geometry and angle of 200°, is, determined by the speed of rotation of the C-arm and the cardiac frequency of the patient, divided into a multiplicity of subareas (hereinafter referred to as fans) of the same size. These fans are precisely so wide that the heart runs through ¼ cardiac phase during their acquisition. This stipulation is based on the fact that for a clean reconstruction of the heart at a particular phase, a maximum phase difference of 0.125 must be present.

The width of a fan (angle $\alpha_{fan}$) can be determined via the formula $$\alpha_{fan} = \frac{\text{Rotation speed}}{4 * \text{cardiac frequency}} = \frac{n_{FPS} * \text{Angulation\_Step}}{4 * \text{cardiac frequency}}$$

where $n_{FPS}$ represents the number of images per second and

Angulation_Step represents the angular increment of the recordings.

This allows us to calculate, for example, that at a rotational speed of 80°/s and a cardiac frequency of 60 beats per minute, a fan width of 20° is required in each case.

Through this finding it is possible to determine the number of fans required for an entire acquisition.

$$n_{fan} = \frac{acquisition area}{\alpha_{fan}}$$

In the example cited, the whole recording area is thus divided into 10 fans of 20° each. Of course this quotient need not always be an integer, so that a subfan can occur in the final phase of a forward motion.

1.2. Assignment of the Fan to the Runs

The number of fans determined earlier must now be distributed over the two C-arm planes in such a way that after forward and backward motion a complete coverage with recordings for matching cardiac phases is guaranteed. It has been shown that a cyclical, sequential arrangement sequence "C-arm plane-A—forward motion|C-arm plane-A—backward motion|C-arm plane-B—forward motion|C-arm plane-B—backward motion" proves to be optimal.

Figure 3:
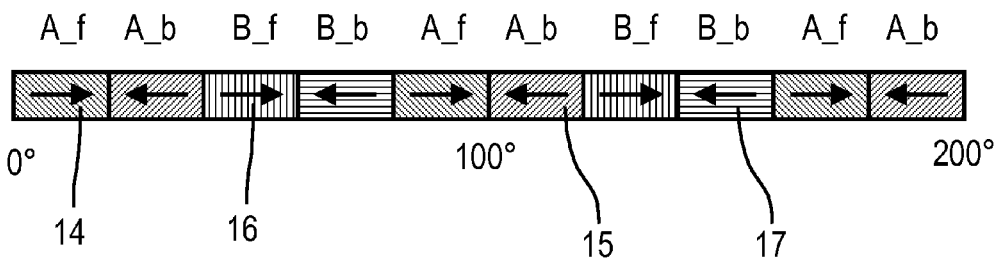

In the cited example this would mean that, as shown in simplified fount in FIG. 3, the C-arm plane A in the forward motion (A_f) correctly covers the fan 14 and in the backward motion (A_b) the fan 15. The C-arm plane B would at the same time acquire the fan 16 in the forward motion (B_f) and the fan 17 in the backward motion (B_b). After the two C-arm planes perform the same rotational movement, the C-arm plane B would theoretically also record the 11th and 12th fan, which are not shown. However this need not necessarily be performed with irradiation, as these are no longer required for the reconstruction. Graphically, the distribution can be represented in linear form as follows. FIG. 3 shows, in a compact representation, the distribution of fan distribution over the entire scan area. A and B indicate the C-arm planes. The C-arm plane suffix_f here describes the forward motion (forward-run), _b the backward motion (backward-run).

1.3. Marginal Conditions for the Two C-Arm Planes 1.3.1. Intermediate Angle Between the C-Arm Planes The paired assignment of the fan to the individual C-arm planes gives rise to a first marginal condition:

The C-arm plane B must commence the acquisition of two fans after the C-arm plane A. Consequently, the intermediate angle between the two C-arm planes must be precisely two fans in size $$\alpha_{intermediate\ angle} = 2 * \alpha_{fan}.$$

As a result of the properties of the recordings being performed at particular angular values defined by the angular increment, this intermediate angle can be limited to a fixed number of "digital angular values" (multiples of the ang. increment), in order always to achieve simultaneous acquisition with the two C-arm planes. Thus the intermediate angle of the example presented in the solution approach with an angular increment of 0.8°/frame would amount to precisely 40°, but with an angular step-width of 1.5°/frame to 40.5°. As a result, the formula previously introduced for the start intermediate angle would change, at a minimum to $$\alpha_{intermediate\ angle} = \left\lceil \frac{2*\alpha_{fan}}{Angulation\_Step} \right\rceil * Angulation\_Step$$

The formula describes a definition of the intermediate angle $\alpha_{intermediateangle}$ by means of a digital graduation of the possible values. The step-width of the graduation is defined by the Angulation_Step; this describes the rotation of the C-arm between two recordings. The next higher, possible angular value is used in all cases; the intermediate angle is thus quantized or rounded up to the next higher value.

If it should be impossible or undesirable for acquisition of the two C-arm planes to take place at identical points in time (for example for reasons of scattered radiation between two active tubes), this intermediate angle can be adjusted accordingly, without this having any effect on the actual acquisition (in the minimally "delayed" acquisition time, the cardiac phase changes to a scarcely measurable extent). In this case a corresponding offset would need to be added to the intermediate angle (and thus a change in the start angle of a C-arm plane), in order to achieve a slightly longer running time up to the acquisition angle.

1.3.2. Handling of Intermediate Angles not Realizable by Mechanical Means

However through the use of the new technologies certain difficulties arise which cannot be alleviated through structural/mechanical means. A minimum intermediate angle between the two C-arm planes thus applies below which it must be reached (because for example collisions involving the detectors or contact between the C-arms may otherwise occur).

As a result of this limitation it is necessary, in the case of fans which are smaller that half of the min. intermediate angle, to insert what are known as "free fans". Their number can be determined through the use of the following equation, in which the quotient between the min. intermediate angle and the doubled fan angle (that is the area covered by the first C-arm plane) is rounded up to the whole number value (integer):

$$n_{free\ fans} = \left\lceil \frac{min.\ intermediate\ angle}{2*\alpha_{fan}} \right\rceil$$

The second C-arm plane is thereby only started at an intermediate angle of $$\alpha_{plane2} = (4*n_{free\ fan} + 2)*\alpha_{fan}$$

Furthermore, these free fans give rise to an area for which no matching image acquisitions are performed. This fact in turn requires an increase in the overall angle of rotation.

As a result of the dependence on the fan width, and thus also on the cardiac frequency of the patient, this position of the C-arm planes relative to each other varies, and a brief "orientation phase" is necessary at the start of the acquisition.

In the case of unfavorable fan sizes it can thus happen that the minimal possible intermediate angle is very slightly greater than the necessary distance. An offset angle of almost 3*"min. intermediate angle" is therefore necessary.

In the case of a system in which the minimum intermediate angle amounts to 25°, this can increase to a 75° intermediate angle. As a result of the increased intermediate angle and the need for acquisition of a fully covered 200° path, it is necessary then to carry out a complete recording over an angular area of 250°, in order to use the areas between 50° and 250° for the reconstruction (which then has been completely recorded). The C-arm plane A here traverses the angular area between 0° and 250° and the C-arm plane B in turn between 75° and 325°.

Figure 4:
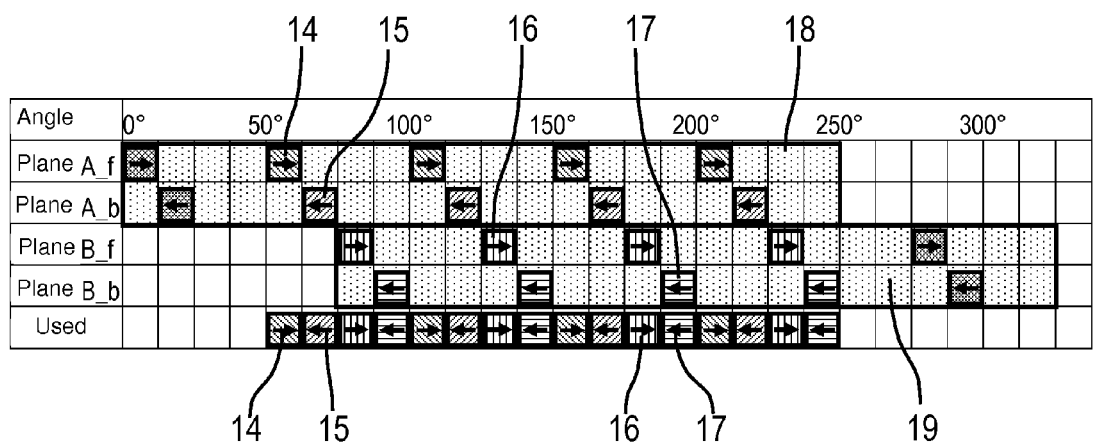

FIG. 4 illustrates how the acquisition takes place. The acquisition angle is entered in the top line. The acquisitions of the fan 14 can be taken from the second line, which corresponds to the C-arm plane A in forward motion (A_f). In the third line are entered the acquisitions of the fan 15, which corresponds to the C-arm plane A in backward motion (A_b). The next line contains the acquisitions for fan 16, which corresponds to the C-arm plane B in forward motion (B_f). In the fifth line are entered the acquisitions for fan 17, corresponding to the C-arm plane B in backward motion (B_b). The last line indicates which of the fans 14 to 17 are used for reconstruction purposes.

FIG. 4 now represents the worst-case scenario of the acquisition and makes clear how the reconstruction areas used in this case are put together, these being specified in the bottom line and corresponding to fans 14 to 17. The extremely unfavorable intermediate angle of 75° gives rise to trajectories of [0°; 250°] and [75°; 325°]. The angular areas 18 and 19 are indicated by dotted lines in FIG. 4. The individual C-arm planes thus rotate in each case through an angular area 18 or 19 respectively, of 250°. Acquisition areas not incorporated into the reconstruction are shown as dark areas. No radiation is called for in these areas.

As a rotation through 200°+2*"min. intermediate angle" (in the cited example 250°) appears to be scarcely realizable for both C-arm planes, a further optimization of the technology is described below, which permits a reduction of the value to 200°+"min. intermediate angle" (corresponds to 225° in the case presented).

1.4. Optimization of the Runs to the Smallest Possible Angular Area

In order to prevent excessive "play" in the movement between the C-arm planes and thus also a very large traversable angular area, another technical possibility is set out below that enables reduction of the angle to 200°+"min. intermediate angle".

This change succeeds by simply switching the sequence of fan assignment to C-arm plane A and C-arm plane B, so that from now on the C-arm plane B is assigned fan 1 and 2. These fans are then used as free fans and C-arm plane B begins at an intermediate angle of $$\alpha_{planeB} = (4*n_{free\ fan})*\alpha_{fan}.$$

This change can furthermore also be implemented for the starting times of the runs by simple algorithmic means through a change in the(pseudo)desired cardiac phase by 0.5, as the C-arm plane A then begins with "unnecessary angular areas" and the desired cardiac phase occurs only in the fan 3 (and then also for acquisition purposes).

The angular areas between "min. intermediate angle" and 200°+"min. intermediate angle" are then used for reconstruction purposes.

In order to prevent an additional radiation exposure of the patient, the tubes should apply no radiation in areas lying outside the reconstruction area.

Figure 5:
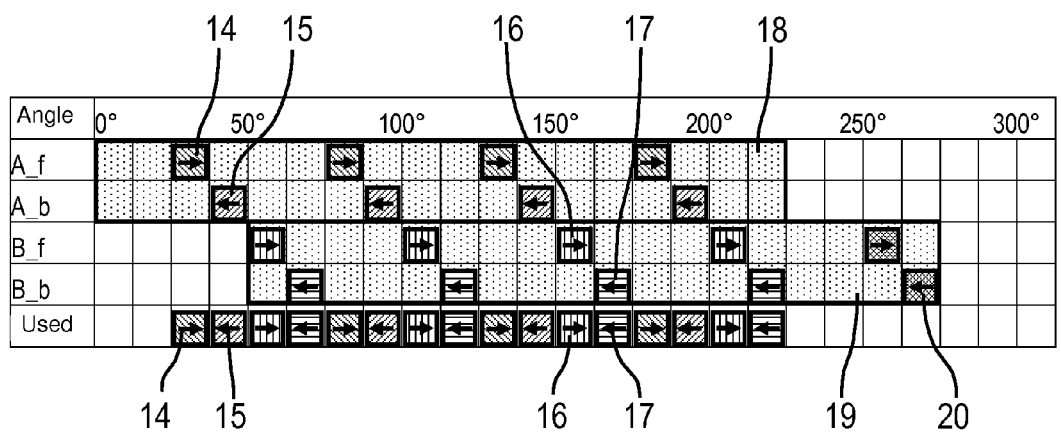

FIG. 5 shows the worst-case of the optimized variant. The changed beginning of the acquisition is evident, along with the resultant intermediate angle of now just 50° and the rotation requirement of only 225°. The same representational rules apply as in FIG. 4.

1.5. Starting Times of the Runs

The starting times of the runs constitute the elementary foundation of the biplane MUX technology. They specify the cardiac phase at which the forward and backward motion is to commence.

In individual terms, the following formulae emerge:

$$\tau_{Heart,Forward} = \left(\tau_{REC} - \frac{\tau_{Delta}}{2}\right) \bmod 1$$

$$\tau_{Heart,Backward} = (2*\tau_{REC} - \tau_{Heart,End\_Forward} + \tau_{Delta}) \bmod 1$$

where the variables used stand for the following elements:
$\tau_{Heart,Forward}$: Start-cardiac phase of the forward motion,
$\tau_{Heart,Backward}$: Start-cardiac phase of the backward motion,
$\tau_{REC}$: The desired cardiac phase of the 3-D-reconstruction,
$\tau_{Delta}$: The width of the acceptance area around the desired cardiac phase of the 3-D-reconstruction (generally 0.25) and
$\tau_{Heart,End\_Forward}$: Cardiac phase at the end of the forward motion.

Reference is once again made to the optimization findings of the previous section and it is here reiterated that in some cases it may be necessary, for determining the starting times, to change the desired reconstruction cardiac phase $\tau_{REC}$ by the value 0.5, and then to calculate modulo 1, in order to guarantee an optimal process.

1.6. Inventive First Solution

By taking account of all marginal conditions previously presented it is possible to realize a 3-D-Cardiac acquisition with the aid of a biplane system with just two runs—one forward and one backward motion. The temporal resolution achieved, and this includes secondary reconstructions for other cardiac phases, is comparable to the monoplane solution currently used. However through the use of the technology proposed here, the acquisition time can be almost halved.

In order also to minimize the calibration effort, it is recommended always to perform acquisition over an angular area of 0 to 200°+"min. intermediate angle", but only to use the area between "min. intermediate angle" and 200°+"min. intermediate angle" for reconstruction purposes. Here it is necessary to use a dynamic area of 200°+2*"min. intermediate angle" for the "adjustable" C-arm plane and for the reconstruction to extract the appropriate projection tables. The acquisition of the C-arm plane, which will always run in the same way, (plane B) need only be calibrated over 200°+"min. intermediate angle", as it always traverses the identical path.

1.7. Temporal Resolution

The temporal resolution of the new variants is equivalent to the previously defined cardiac phase of the solution currently used. However the same result is achieved as previously, but in around half the time.

The reconstructions for the desired cardiac phase (primary reconstruction) are gained from projections whose cardiac phases lie evenly distributed around the desired cardiac phase. The extent of the divergence from the target phase amounts to ±0.125 cardiac phases. Secondary reconstructions for other cardiac phases always lead to one of just four different cardiac phase reconstructions. As a result of the distribution of the cardiac phases over the individual images there are just four cases which are actually reconstructed, specifically all cardiac phases that satisfy the equation $$E_{real\_REC} = (\tau_{REC} + n*0.25) \bmod 1$$

The distribution of the cardiac phase errors of the recordings used for secondary reconstruction always amounts to a width of 0.25 cardiac phases; the center shifts, however, so that in the optimal case, in which the desired cardiac phase tallies with the center of the distribution, there is an error distribution of [−0.125; 0.125] and in the worst case, where the desired cardiac phase lies at the edge of the distribution, a distribution of [−0.25; 0.0] or [0.0; 0.25] cardiac phases. The center always remains at a cardiac phase determined by $\tau_{real\_REC}$.

2. Second Inventive Solution Approach

Contrary to the first inventive solution, a uniform geometric position of the C-aim planes relative to each other, that is a fixed intermediate angle, is a prerequisite. In order to achieve this, the speed of rotation of the C-arms is treated as a variable. This marginal condition ensures that, compared with the first inventive solution, no additional waiting time for alignment of the C-arm planes is required. Furthermore, the rotational paths are always the same; no extra calibration effort is therefore required. Additionally as a result of this second inventive acquisition the smallest possible rotation of the C-arm planes is to be required, as it appears to be problematic to achieve rotatability of significantly more than 200° with the second plane.

In the second inventive solution too the problem is addressed by means of a fan-like distribution of the recording area into angular areas of the same size. These angular areas are then assigned to the different C-arm planes in a selective manner and linked to form an overall acquisition through coordinated dovetailing (Multiplexing) of the individual recordings. By means of this technique it is possible in future to realize a recording equivalent in quality to DynaCT Cardiac with just two runs instead of with four, using both C-arm planes. The C-arm planes for their part rotate simultaneously at the same speed of rotation in the same direction; they accordingly have a fixed angle to each other, hereinafter referred to as an intermediate angle This angle is, however, subject to a limitation at the lower end due to the mechanical construction of the C-arm planes, so that it is not possible to achieve angles of any minimum size desired.

As a result of the variable speed of rotation of the C-arm according to the second exemplary embodiment it is possible to set this intermediate angle at a fixed value. The advantage of this solution clearly lies in the fact that the trajectory of the C-arm planes always remains the same; nevertheless the system must always be in a position, in the case of a fixed angular increment, to deal with an acquisition rate of a different level.

2.1. Fan Definition

Here too, the whole recording area, due to the fan beam geometry an angle of 200°, is divided into a multiplicity of subareas or fans of the same size, which must be precisely of a size such that during their acquisition the heart runs through ¼ cardiac phase. This stipulation is based on the fact that for a clean reconstruction of the heart at a particular phase, the max. phase difference that may be present is 0.125. With a fixed, prescribed intermediate angle of the C-arm planes this width depends solely on this intermediate angle, and amounts to half of the intermediate angle. The size of a fan (Angle $\alpha_{fan}$) can be determined via the formula $$\alpha_{fan} = \alpha_{planes}/2$$

where $\alpha_{planes}$ corresponds to the fixed intermediate angle between the two C-arm planes. It is, for example thus possible to calculate that in the case of an intermediate angle of 40° a fan width of 20° is necessary. In order to achieve the complete coverage required for a clean reconstruction, it is, as previously mentioned, necessary to traverse precisely ¼ of the cardiac phase in this fan area. As a result of the varying cardiac frequency between different patients it is possible to conclude that the speed of rotation of the C-arm must be adjusted to the cardiac frequency. The C-arm must be in a position to traverse four fans within one heartbeat. In the abovementioned example this means that the system in the case of a cardiac frequency of 60 beats per minute (1 Hz) must have a speed of rotation of 80°/s (with an angular increment of 1.5° this corresponds to an acquisition rate of 53.33 images per second (fps)). At an increased cardiac frequency of 80 beats per minute an angular speed of 106.66°/s (an image rate of 71 fps) would in turn be necessary. At first sight this appears somewhat high; it must, though, be taken into account that for example by means of the use of β-blockers as is customary in computer tomography a significant reduction in cardiac frequency can be achieved and thus recordable areas attained without problems. As a result of the division of the angular areas into fans of static width, the number of fans necessary for a complete acquisition can be regarded as fixed.

$$n_{fan} = \frac{\text{Acquisition area}}{\alpha_{fan}} = \frac{200°}{\alpha_{fan}}$$

In the example cited, the entire recording area is thus divided into 10 fans of 20°.

2.2. Assignment of the Fan to the Runs

The number of fans determined as above must now be divided between the two C-arm planes, such that after a forward and backward run, complete coverage with recordings for matching cardiac phases is guaranteed. It has proved to be the case that a cyclical, sequential arrangement sequence "C-arm plane-A—forward motion|C-aim plane-A—backward motion|C-arm plane-B—forward motion|C-arm plane-B—backward motion" emerges as optimal, as has already been explained for example on the basis of FIG. 3.

2.3. Optimization of the Runs to the Smallest Possible Scan Angular Area

Further optimization possibilities to achieve the best possible use of the available options are created through the fixed division of the angular area into $n_{fan}$ fans of the same size. This ensues if as few "free fans" as possible, that is regions in which no radiation takes place, are present. Division into a multiple of four fans represents the optimum situation, as no "free motion" of C-arm planes then takes place and both C-arm planes always acquire data. It emerges from this that only a few angular values appear to be sensible for the intermediate angle:

100°: tends to be unrealistic, as the speed of rotation of the C-arm must be too high.
50°: practicable, though a very high speed of rotation is still necessary.
33.33°: optimal.
25°: optimal, if realizable.

These solutions achieve the minimum scan area of $\alpha_{rotation}=200°-\alpha_{planes}$, that is for example to 166.66°, but are subject to very exacting requirements.

Figure 6:
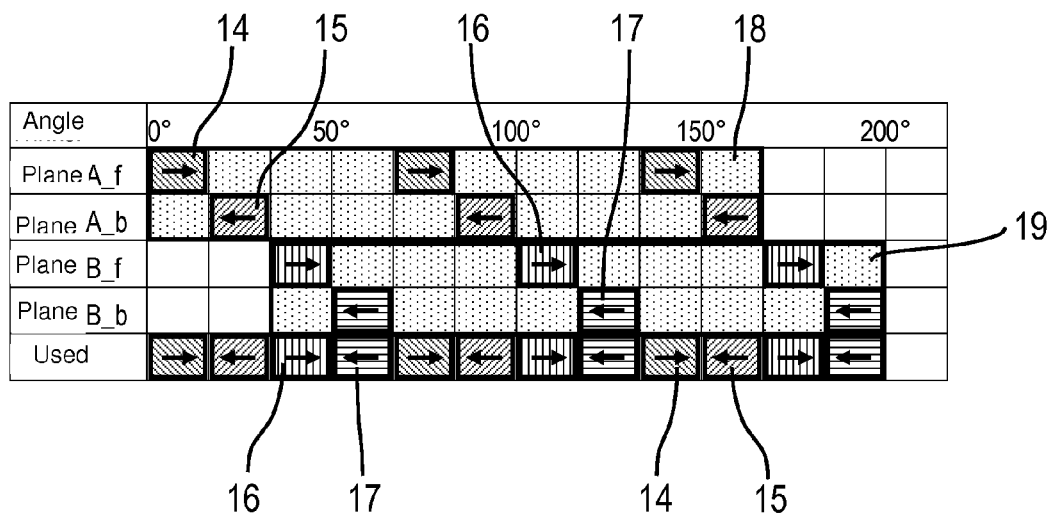

FIG. 6 shows an optimal case of distribution for an intermediate angle of 33.33° and the resultant overall angle of rotation of 166.66°.

As an alternative to this best optimization, a so-called "mixed solution" also presents itself, which requires only one free fan. This is achieved by dividing the entire scan area into 4*χ−1 fans. From this only a few, sensible values for the intermediate angle (double fan width) then again arise:

57.14°: very high speed of rotation necessary.
36.36°: optimal.
26.67°: optimal, if angle can be realized.

By means of this solution a reduction of the rotational area $$\alpha_{rotation} = 200° - \frac{\alpha_{planes}}{2},$$

that is for example to 181.82°, is possible.

Figure 7:
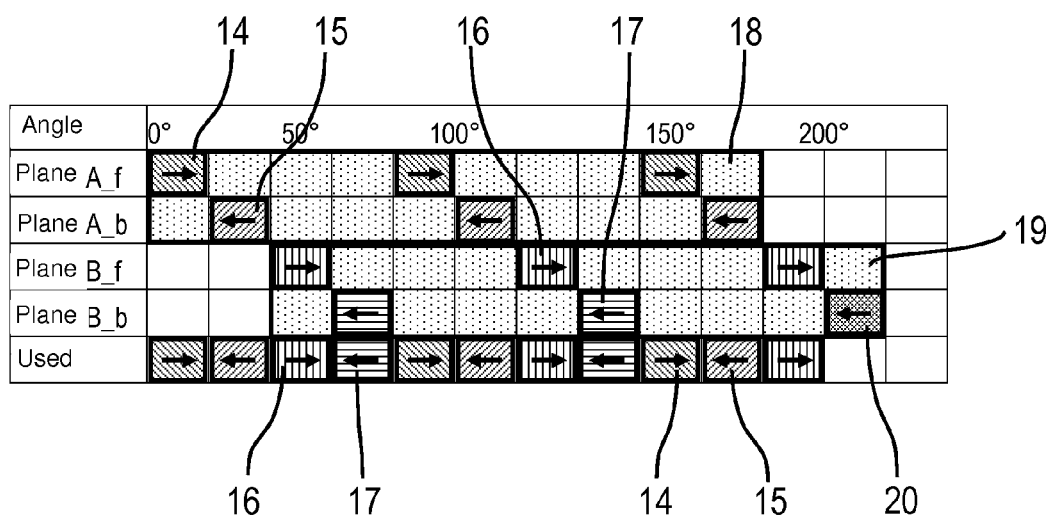

FIG. 7 represents a "mixed solution" of this kind, in which a fan remains unused. Marginal conditions here are an intermediate angle of 36.36° and a resultant overall angle of rotation of 181.82°.

2.4. Speed of Rotation of the C-Arm

As a result of the requirement to acquire a fan in precisely ¼ of a heartbeat, the following conditions arise for the speed of rotation $\omega_{speed\ of\ rotation}$ of the system:

$$\omega_{speed\ of\ rotation}=4*\alpha_{fan}*\text{cardiac frequency,}$$

so that for example at a cardiac frequency of 60 beats per minute and a fan width of 16.66° a necessary speed of rotation of 66.66°/s arises.

2.5. Time Requirement for the Acquisition Run

As a result of the variable speed of rotation of the C-arm employed in the second solution approach, acquisitions of different durations are of course produced, depending on the cardiac frequency of the patient. In this invention the total time is made up in each case of a forward and backward movement at the same speed plus the waiting times before the start of the rotations. The necessary total time span t can be determined by the following formula:

$$t_{total} = 2 * \frac{\alpha_{rotation}}{\omega_{speed\ of\ rotation}} + t_{wait,1} + t_{wait,2}$$

where $t_{wait,1}$ corresponds to the waiting time before the first start and $t_{wait,2}$ is the waiting time before the start of the reverse motion of the system.

The waiting times before the start of the individual runs can in turn in the worst-case scenario be laid down in each case with one cardiac phase, so that thereby for example with a cardiac frequency of 60 beats per minute an overhead of two seconds would arise as a result of the waiting times (in each case a maximum of one complete heartbeat (1 s) before each run). The entire acquisition would then, for example at an intermediate angle of 33.33° (the optimum case, see above, with a rate of rotation of 66.66°/s and 60 bpm), take place over a period of seven seconds. Compared with the monoplane-solution currently used, which requires four runs each of five seconds (thereby giving in the worst-case scenario a time requirement of 24 seconds), this method represents a significant speeding-up of recording. It must be noted, though, that to date a fixed rate of rotation of 40°/s has been employed, while the new method calls for variable, higher rates of rotation.

2.6. Starting Times of the Runs

In the case of the second solution approach too what has already been mentioned under point 1.5 in relation to the starting times of the runs applies.

2.7. Inventive Second Solution

By taking account of all previously described marginal conditions it is possible to realize a 3-D cardiac acquisition with the aid of a biplane-system with just two runs, one forward and one backward motion. The achievable temporal resolution of the primary reconstruction, that is at the prescribed cardiac phase $\tau_{REC}$, is comparable with the monoplane solution currently used. The acquisition time can however be significantly reduced by means of the technique proposed here.

Thanks to the possibility of adjusting the rate of rotation of the system to the patient dynamically, there emerge as yet unconsidered possibilities and marked advantages for the acquisition compared with other cardiac-biplane techniques. Through the optimum layout of the fans and their distribution, a reduction in the overall rotational area, depending on the intermediate angle, can be achieved.

From the current perspective, the selection of an intermediate angle von 33.33° and the resultant division of the 200°-reconstruction area into twelve fans each of 16.66° is advisable.

This selection gives rise to the following requirements relating to the C-arm systems:
Both C-arm planes must be able to cover an angular area of 166.66°.
The speed of rotation must be in a position to move in regions of up to ~100°/s:
A cardiac frequency of 40 beats per minute requires a rate of rotation of 44.44°/s.
At a cardiac frequency of 60 beats per minute a rate of rotation of 66.66°/s is called for.
At a cardiac frequency of 80 beats per minute a rate of rotation of 88.88°/s is required.
A cardiac frequency of 90 beats per minute presupposes a rate of rotation of 100°/s.

This choice further produces a significant advantage in the overall acquisition time.

Depending on the cardiac frequency of the patient, the following maximum times can be determined:

|  | Cardiac frequency | | | |
| --- | --- | --- | --- | --- |
|  | 40 bpm | 60 bpm | 80 bpm | 90 bpm |
| Max. delay per run | 1.5 s | 1 s | 0.75 s | 0.6 s |
| Rotation time per run | 3.75 s | 2.5 s | 2 s | 1.66 s |
| Rate of rotation | 44.44°/s | 66.66°/s | 88.88°/s | 100°/s |
| Total time | 10.5 s | 7 s | 5.5 s | 4.52 s |
| Monoplane solution with 40°/s or with "new" rate of rotation | 26 s/24 s | 24 s/16 s | 23 s/12 s | 22.4 s/10.4 s |
| Saving | 59.6%/56.3% | 70.8%/56.3% | 76%/54.2% | 79.8%/56.5% |

The temporal advantage of this solution thereby achieved amounts, in effectively all conceivable cases, to more than 50%, that is the acquisition time is more than halved.

Nevertheless, attention is once again drawn to the fact that the previous solution is only implemented with a rate of rotation of 40°/s, while the new variant presupposes a variable, significantly higher angular frequency. For this reason, determination of the maximum acquisition duration for the previous method using the rate of rotation adjusted in each case for the new method has also been performed for comparison purposes.

2.8. Temporal Resolution

The temporal resolution of the new variant is equivalent to the previously defined cardiac phase of the solution currently used. However the same result is achieved in less than half the time than previously.

The reconstructions for the desired cardiac phase (primary reconstruction) are gained from projections whose cardiac phases are evenly distributed around the desired cardiac phase. The size of the divergence from the target phase amounts to ±0.125 cardiac phases.

Secondary reconstructions at a cardiac phase that differs from the cardiac phase selected upon the recording, are of course likewise possible, as with other methods. Here though, more substantial divergences can occur through the use of interpolation at the edges of the recording area, as matching projections are not always available. Compared with other methods, this can in turn result in lower quality of the reconstructed volume. An improvement in quality would require complete coverage of a 200° rotational area in each case with four projections at different cardiac phases, which is only realizable through an overlapping rotational area of 200°. (This would call for an angle of rotation of 233.33° in the case of an intermediate angle of 33.33°).

3. Significant Features and Advantages of the Inventive Solutions

A significant factor for the inventive method is the interlacing of the individual acquisition areas in a "fan arrangement", which can also be designated fan-multiplexing, and their optimum arrangement for the forward and backward motion of the 3-D-CARD acquisition, in order to achieve the best possible coverage. A reconstruction of the heart at a desired cardiac phase can thereby be realized, and secondary reconstructions also continue to be possible.

This invention furthermore also takes account of marginal conditions such as the min. intermediate angle between two C-arm planes.

Likewise significant for the inventive method is the dynamic adjustment of the speed of rotation of the system to the cardiac frequency of the patient, of an optimum interlacing of the individual acquisition areas in a fan-multiplexing derived therefrom, and their optimum arrangement for the forward and backward motion of the 3-D-CARD—acquisition for attainment of the best possible coverage. A reconstruction of the heart at a desired cardiac phase can thereby be realized.

The present patent application has the following advantages:

Through the use of both available C-arm planes for a cardiac acquisition the data throughput of the acquisition is doubled and the overall acquisition time can thereby be significantly reduced, for example halved.

Despite this accelerated data recording scarcely any disadvantages are incurred for the reconstruction. The same temporal resolution is achieved as in the previous method, with its longer duration. For secondary reconstructions at other cardiac phases too, there are no or only minor qualitative changes.

Furthermore, the more rapid recording time reduces the risk that the patient moves during the acquisition, thus preventing possible movement artifacts. Also, as a result of the shorter procedure, the administering of contrast medium which may be necessary can be curtailed and limited.

For the patient then, significantly less stress is incurred, as a result of the reduced recording times.

In the case of the second inventive solution in secondary reconstructions at a different cardiac phase the quality can, though, deteriorate somewhat. This disadvantage arises as a result of the reduced rotational requirement of the C-arm of, for example, 166.66°. This reduced rotational requirement does, however, above all represent a huge advantage from the mechanical/structural perspective, and additionally ensures a further speeding-up of the acquisition. Additionally, as a result of the more rapid recording time, there is less danger that the patient will move during acquisition, and possible movement artifacts are thus prevented. Also, as a result of the shorter procedure, the administering of contrast medium which may be necessary can be curtailed and limited. As a result, of the vastly reduced recording times, the patient is subjected to significantly less exposure.

4. Representations of Exemplary Embodiments

Course of a first embodiment of a complete 3-D-Card-MUX acquisition

The course of a 3-D-CARD acquisition on a biplane-system takes the following form according to the present patent application:

Determining of the cardiac frequency of the patient.
The intermediate angle of the C-arm planes calculated therefrom is commenced through movement of C-arm plane A.
As soon as the alignment is completed, the calculated start-cardiac phase is awaited and the acquisition of the data commences upon its occurrence.
Both C-arm planes rotate uniformly at the same speed over an angular area of 200°+"min. intermediate angle" and record different angular areas of the patient at different cardiac phases.
After termination of the forward motion, the C-arms wait until the start cardiac phase of the backward motion, and are set in motion upon its occurrence.
After the end of the backward motion the acquisition is completed and the captured data can be reconstructed.

4.1.1. Sample Representation of Cardiac Phase Distribution

Figure 8:
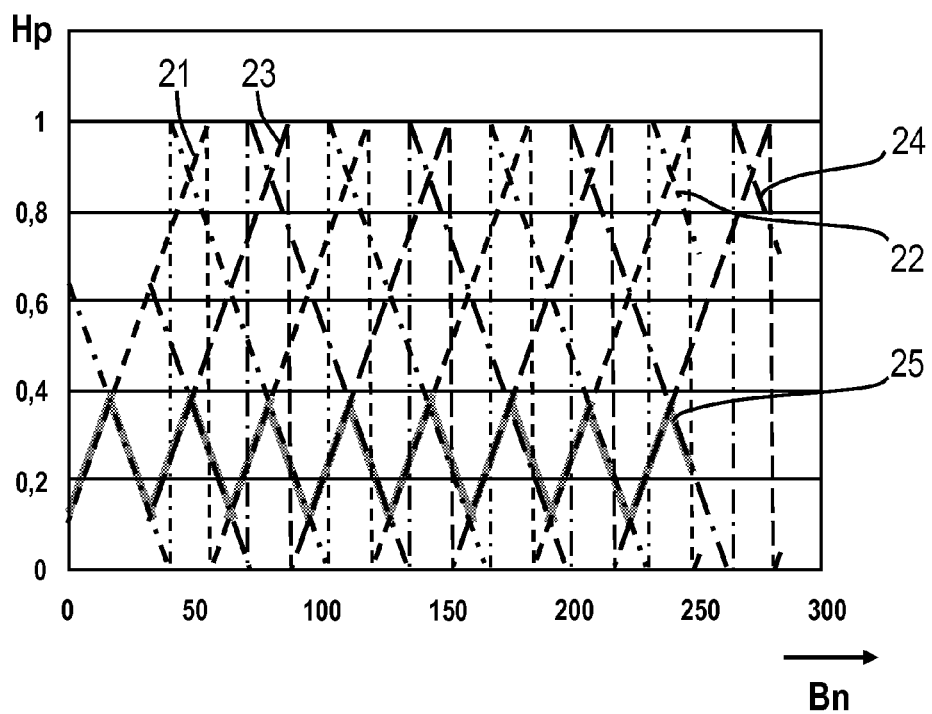

In FIG. 8 is represented a sample plot of the result of the simulation of a biplane acquisition according to the first solution approach. It shows the distribution of the cardiac phases across the individual acquired images and thus also the division over the angular areas of the scan.

The simulation run according to FIG. 8 has been based on a desired reconstruction time $\tau_{REC}=0.25$ at a cardiac frequency of 47 bpm, that is approx. four cardiac phases with five seconds recording time. The x-axis gives the number of images, in this case 250 frames with a 200° recording area, so that 0.8°/f is the angular increment.

The dashed curve 21 describes the forward motion of C-arm plane A, the dashed-and-dotted curve 22 the backward motion. In the case of C-arm plane B, this applies correspondingly to both plots; die long-dashed curve 23 describes the forward motion of C-arm plane B, the long-dashed-and-dotted curve 24 the backward motion. The emboldened curve 25 describes as the result the value used for reconstruction or the cardiac phase used.

4.1.2. Histogram of the Cardiac Phases Used for Reconstruction

There follows a brief introduction and explanation of a sample histogram. This shows that the new methods deliver the same quality as previous systems at almost double the recording speed.

Figure 9:
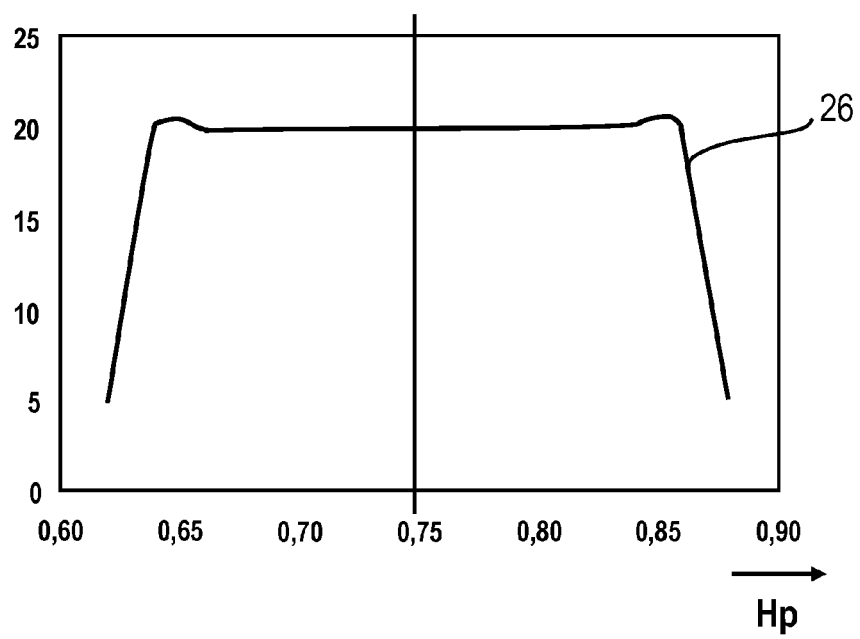

FIG. 9 represents the distribution of the cardiac phases used for primary reconstruction. The primary reconstruction took place at the desired cardiac phase von 0.75. It is evident that the distribution is approximately rectangular, that is all "usable cardiac phases" are incorporated into the reconstruction on an equal basis. In the case of current monoplane acquisitions, for example the aforementioned DynaCT Cardiac Software, the distribution is equivalent. A reconstruction of the same data record at the cardiac phases {0; 0.25; 0.5} would likewise lead to the same optimum distribution pattern.

4.2. Course of a Further Inventive Complete 3-D-Card-MUX Acquisition

The course of a 3-D-CARD acquisition on a biplane system takes the following form, according to a second embodiment of the present patent application:

Determining the cardiac frequency of the patient.
From this is determined the speed of rotation of the entire system.
The calculated start cardiac phase is awaited, and the acquisition of the data commences upon its occurrence.
Both C-arm planes rotate uniformly at the same speed over an angular area of 200°–"intermediate angle" and record different angular areas of the patient at different cardiac phases.
After termination of the forward motion, the C-arms wait until the start-cardiac phase of the backward motion occurs, and are set in motion upon its occurrence.
After the end of the backward motion the acquisition is completed and the captured data can be reconstructed.

4.2.1. Sample Representation of the Cardiac Phase Distribution

Figure 10:
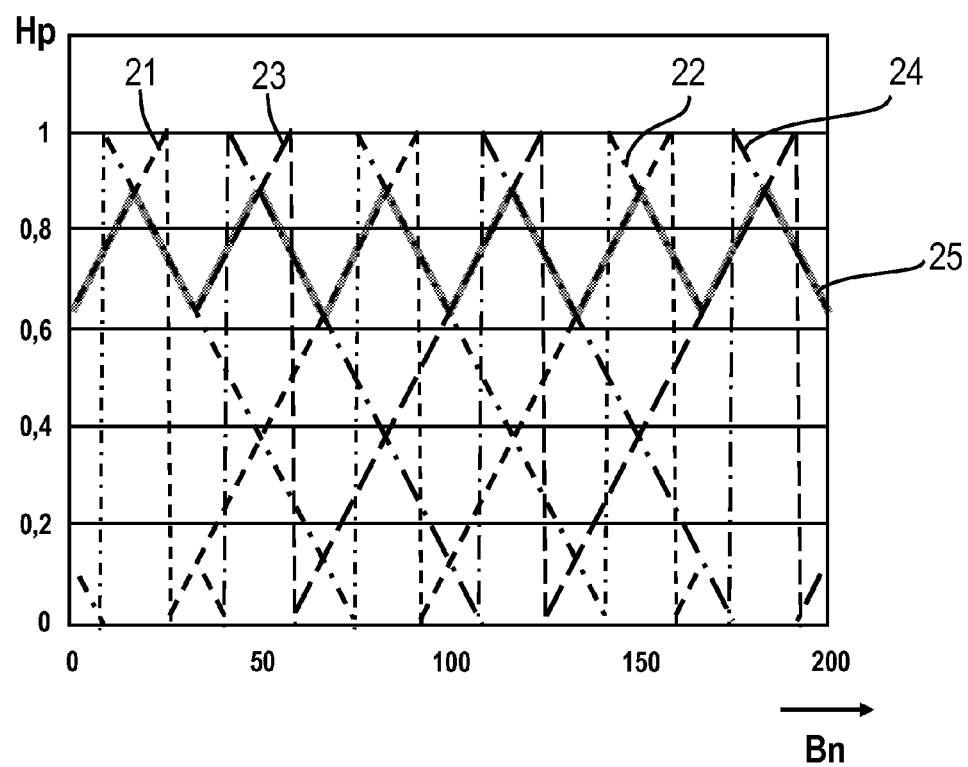

FIG. 10 represents a sample plot of the result of the simulation of a biplane acquisition described here according to the second solution approach. It shows the distribution of the cardiac phases over the individual acquired images and thus also the distribution over die angular areas of the scan.

A desired reconstruction time $\tau_{REC}=0.75$ is based on the simulation run according to FIG. 10 at a cardiac frequency von 60 beats per minute. The recommended value of 33.33° was selected as an intermediate angle between the two C-arm planes.

The same method of representation has been chosen as for FIG. 8.

4.2.2. Histogram of the Cardiac Phases Used for Reconstruction

There follows a brief examination of the sample histogram reproduced in FIG. 9, which makes clear that the new method delivers the same quality as the previous method at a significantly increased recording speed.

FIG. 9 shows the distribution of the cardiac phases used for primary reconstruction, which took place at the desired cardiac phase of $\tau_{REC}=0.75$. It is evident that the distribution is approximately rectangular and symmetrical around the desired cardiac phase, that is all "usable cardiac phases" are incorporated into the reconstruction on an equal basis. Here too it is the case that with current monoplane acquisitions, for example the aforementioned DynaCT Cardiac Software, the distribution is equivalent. For a secondary reconstruction at a different cardiac frequency, the histogram would differ significantly from this symmetrical, trapezoidal form.

By means of the inventive method it is possible for acquisitions using both C-arm planes to be speeded up and thus the investigation time considerably shortened.

The invention claimed is:
1. A method for collecting a three-dimensional data of an object to be examined from a series of projection images of the object recorded by a biplane C-arm system having two separate C-arm planes, comprising:
recording a cardiac activity of the object by an ECG;
determining a cardiac frequency and a start cardiac phase;
calculating parameters of the two C-arm planes from the cardiac frequency and the start cardiac phase;

setting the C-arm planes with the parameters;
acquiring data in the start cardiac phase after setting of the parameters;
uniformly rotating the two C-arm planes at a speed in a forward motion over an angular area;
acquiring data at different angles in the angular area in different cardiac phases during rotating in the forward motion;
acquiring data in the start cardiac phase after terminating the forward motion;
uniformly rotating the two C-arm planes at the speed in a backward motion over the angular area;
acquiring data at the different angles in the angular area in the different cardiac phases during rotating in the backward motion; and
reconstructing all of the acquired data for collecting the three-dimensional data of the object after terminating the backward motion upon completed acquisition,
wherein the two separate C-arm planes are spaced by a fixed intermediate angle between each other.

2. The method as claimed in claim 1, wherein the two C-arm planes are aligned in the start cardiac phase.

3. The method as claimed in claim 1, wherein the angular area is from 0° to 200° plus minimal of the intermediate angle.

4. The method as claimed in claim 1, wherein the angular area is from 0° to 200° minus minimal of the intermediate angle.

5. The method as claimed in claim 1, wherein the speed for rotating the two C-arm planes is calculated.

6. The method as claimed in claim 1, wherein the two C-arm planes are rotated over the angular area in a cyclical and a sequential arrangement.

7. The method as claimed in claim 6, wherein the two C-arm planes are rotated over the angular area in the cyclical and the sequential arrangement of:
rotating one of the two C-arm planes in the forward motion,
rotating the one of the two C-arm planes in the backward motion,
rotating another one of the two C-arm planes in the forward motion, and
rotating the another one of the two C-arm planes in the backward motion.

8. The method as claimed in claim 1, wherein the fixed intermediate angle equals two fans.

* * * * *